(12) United States Patent
Williams

(10) Patent No.: US 8,269,061 B2
(45) Date of Patent: Sep. 18, 2012

(54) SELECTIVE ABLATION OF DIPLOID EMBRYOS

(75) Inventor: Mark E. Williams, Newark, DE (US)

(73) Assignee: E.I. du Pont de Nmeours and Company, Wilmington, DE (US)

( * ) Notice: Subject to any disclaimer, the term of this patent is extended or adjusted under 35 U.S.C. 154(b) by 0 days.

(21) Appl. No.: 13/251,597

(22) Filed: Oct. 3, 2011

(65) Prior Publication Data
US 2012/0023612 A1    Jan. 26, 2012

Related U.S. Application Data

(62) Division of application No. 12/023,152, filed on Jan. 31, 2008, now abandoned.

(60) Provisional application No. 60/887,828, filed on Feb. 2, 2007.

(51) Int. Cl.
| | |
|---|---|
| A01H 1/02 | (2006.01) |
| A01H 5/00 | (2006.01) |
| C12N 15/82 | (2006.01) |
| C12N 15/55 | (2006.01) |
| C12N 15/56 | (2006.01) |

(52) U.S. Cl. ........ 800/275; 800/287; 800/288; 800/299; 800/303; 800/320.1; 435/199; 435/201

(58) Field of Classification Search .................... None
See application file for complete search history.

(56) References Cited

U.S. PATENT DOCUMENTS

| | | | |
|---|---|---|---|
| 5,412,085 A | 5/1995 | Allen et al. | |
| 5,545,546 A | 8/1996 | Allen et al. | |
| 5,639,951 A | 6/1997 | Bosemark et al. | |
| 6,392,119 B1 * | 5/2002 | Gutterson et al. | 800/278 |
| 6,743,968 B2 | 6/2004 | Dellaporta | |
| 2001/0007154 A1 | 7/2001 | Burgess et al. | |
| 2002/0188965 A1 * | 12/2002 | Zhao et al. | 800/288 |
| 2005/0229269 A1 | 10/2005 | Bright et al. | |

FOREIGN PATENT DOCUMENTS

| | | |
|---|---|---|
| WO | WO 96/39803 | 12/1996 |
| WO | WO 00/37660 | 6/2000 |
| WO | WO 01/64926 | 9/2001 |
| WO | WO 02/085104 | 10/2002 |
| WO | WO 2007/038075 | 4/2007 |

OTHER PUBLICATIONS

Pedro Radi Belicuas et al., Androgenetic haploids and SSR markers as tools for the development of tropical maize hybrids, Euphytica(2007), 156:95-102.

Allen, R.L., and Lonsdale, D.M., Sequence analysis of three members of the maize polygalacturonase gene family expressed during pollen development. (1992) Plant Mol. Biol. 20, 343-345.
Allen, R.L., and Lonsdale, D.M., Molecular characterization of one of the maize polygalacturonase gene family members which are expressed during late pollen development. (1993) The Plant Journal 3, 261-271.
An, G., Mitra, A., Choi, H.K., Costa, M.A., An, K., Thornburg, R.W., and Ryan, R.W. Functional analysis of the 3' control region of the potato wound-inducuble proteinase inhibitor II gene. (1989) Plant Cell 1, 115-122.
Beals, T.P., and Goldberg, R.B., A novel cell ablation strategy blocks tobacco anther dehiscence. (1997) Plant Cell 9, 1527-1545.
Hartley, R.W. Barnase and Barstar: Expression of its cloned inhibitor permits expression of a cloned ribonuclease. (1988) J. Mol. Biol. 202, 913-915.
Hartley, R.W. Barnase and Barstar: Two small proteins to fit and fold together. (1989) Trends Biochem. Sci. 14, 450-454.
Jones, J.D.G., Dunsmuir, P., and Bedbrook, J. High level expression of introduced chimaeric genes in regenerated transformed plants. (1985) EMBO J. 4, 2411-2418.
Mariani , C., De Beuckeleer, M., Truettner, J., Leemans, J., and Goldberg, R.B., Induction of male-sterility in plants by a chimaeric ribonuclease gene. (1990) Nature 347, 737-741.
Mariani, C., Gossele, V., De Beuckeleer, M., De Block, M., Goldberg, R.B., Degreef, W., and Leemans, J. A chimaeric ribonuclease-inhibitor gene restores fertility to male starile plants. (1992) Nature 357, 384-387.
Lotan, T., Ohto, M., Yee, K.M., West, M.A.L., Lo, R., Kwong, R.W., Yamagishi, K,Fischer, R.L., Goldberg, R.B., and Harada, J.J. *Arabidopsis* Leafy Cotyledon1 is sufficient to induce embryo development in vegetative cells. (1998) Cell 93, 1195-1205.
Rogers, H.J., Allen, R.L., Hamilton, W.D.O., and Lonsdale, D.M., Pollen specific cDNA clones from *Zea mays*. (1991) Biochim. Biophys. Acta 1089, 411-413.
Twell, D., Diphtheria toxin-mediated cell ablation in developing pollen: vegetative cell ablation blocks generative cell migration. (1995) Protoplasma 187, 144-154.
Williams, M.E., Leemans, J., and Michiels, F. Male sterility through recombinant DNA technology. In Pollen Biotechnology for Crop Production and Improvement, K.R. Shivanna and V.K. Sawhney, eds (1997) (Cambridge, UK: Cambridge University Press), pp. 237-257.
Debeaujon Isabelle, et al., Poanthocyanidin-Accumulating Cells in *Arabidopsis testa*:Regulation of Differentiation and Roles in Seed Development, (2003) The Plant Cell 15, 2514-2531.

* cited by examiner

*Primary Examiner* — David T Fox

(57) ABSTRACT

Methods of selecting haploid embryos are disclosed. Methods of producing haploid embryos and non-viable diploid embryos on a plant are provided. Methods for selecting haploid embryos produced from haploid inducer maize lines are provided. Methods for producing improved maize haploid inducer lines are disclosed. Maize haploid inducer lines comprising transgenes causing ablated or abnormal diploid embryos are disclosed.

4 Claims, No Drawings

SELECTIVE ABLATION OF DIPLOID EMBRYOS

CROSS REFERENCE TO RELATED APPLICATIONS

This application is a divisional application of U.S. application Ser. No. 12/023,152, filed Jan. 31, 2008 and now abandoned, which claims the benefit of U.S. provisional application 60/887,828 filed Feb. 2, 2007, the entire contents of which are hereby incorporated by reference.

THE INVENTION

The present invention relates to the field of plant breeding and plant biotechnology.

BACKGROUND OF THE INVENTION

Homozygous plants are basic for product development and commercialization of plants. To obtain homozygous plants requires several generations of self-pollination and segregation analysis. This is an inefficient use of labor and time. It would therefore be useful to develop a method to reduce hand pollination steps normally required to obtain a homozygous plant and reduce the amount of time required to obtain a homozygous population of plants. One way to obtain homozygous plants without the need to self-pollinate multiple generations is to produce haploids and then double the chromosomes to form doubled haploids. A process to assist in the selection of haploid embryos and elimination of diploid embryos would increase the efficiency of doubled haploid production.

SUMMARY OF THE INVENTION

Methods for identifying haploids by preventing the growth of diploid embryos are provided. Methods for identifying haploid plants, seeds, embryos, and plant cells are provided. Methods for producing haploid inducer lines and the haploid inducer lines are provided.

DETAILED DESCRIPTION OF THE INVENTION

A haploid plant has a single set (genome) of chromosomes and the reduced number of chromosomes (n) in the haploid plant is equal to that in the gamete.

A diploid plant has two sets (genomes) of chromosomes and the chromosome number (2n) is equal to that in the zygote.

A haploid cell is one with a single genome, male or female.

A doubled haploid or doubled haploid plant or cell is one that is developed by the doubling of a haploid set of chromosomes. A plant or seed that is obtained from a doubled haploid plant that is selfed any number of generations may still be identified as a doubled haploid plant. A doubled haploid plant is considered a homozygous plant. A plant is considered to be doubled haploid if it is fertile, even if the entire vegetative part of the plant does not consist of the cells with the doubled set of chromosomes. For example, a plant will be considered a doubled haploid plant if it contains viable gametes, even if it is chimeric.

A "haploid embryo" is defined as the embryo formed after one sperm nucleus from a pollen grain fuses with the polar nuclei in the embryo sac to create a triploid (3N) endosperm and the embryo forms without the contribution of the male genome.

An "immature haploid embryo" is defined as the embryo formed after one sperm nucleus from a pollen grain fuses with the polar nuclei in the embryo sac to create a triploid (3N) endosperm and before dry down. And the embryo forms without the contribution of the male genome.

A "doubled haploid embryo" is an embryo that has one or more cells that contain 2 sets of homozygous chromosomes.

"Callus" refers to a dedifferentiated proliferating mass of cells or tissue.

The phrases "contacting", "comes in contact with" or "placed in contact with" can be used to mean "direct contact" or "indirect contact". For example, the medium comprising a doubling agent may have direct contact with the haploid cell or the medium comprising the doubling agent may be separated from the haploid cell by filter paper, plant tissues, or other cells thus the doubling agent is transferred through the filter paper or cells to the haploid cell.

The term "medium" includes compounds in liquid, gas, or solid state.

As used herein, the term "plant" includes reference to whole plants, plant organs (e.g., leaves, stems, roots, etc.), seeds and plant cells and progeny of same. "Plant cell", as used herein includes, without limitation, seeds, suspension cultures, embryos, meristematic regions, callus tissue, leaves, roots, shoots, gametophytes, sporophytes, pollen, and microspores.

The haploid inducer line comprises; 1) a pollen lethality polynucleotide or a non-transmission pollen polynucleotide, 2) an embryo lethality polynucleotide, and 3) an embryo lethality repressor.

The pollen lethality polynucleotide or a non-transmission pollen polynucleotide indicates any polynucleotide that prevents the pollen from achieving fertilization. The pollen non-transmission is most effective if it occurs at the post-meiotic or gametophytic stage. The non-transmission pollen polynucleotide can work through various mechanisms. It may prevent the pollen from being viable for example by the expression of a toxic compound.

The embryo lethality polynucleotide is any polynucleotide that prevents proper development of the embryo or causes the embryo to be non-viable. The embryo lethality polynucleotide may slow the growth of the embryo so that one may be able to distinguish an embryo that carries the embryo lethality polynucleotide from an embryo that does not carry the embryo lethality polynucleotide.

The embryo lethality repressor is any polynucleotide that when expressed causes the embryo lethality polynucleotide to be non-effective and allows a viable embryo to develop. This can be achieved through various mechanisms. For example the embryo lethality repressor can detoxify the molecule expressed by the embryo lethality polynucleotide. An embryo repressor protein may be expressed that inhibits the lethality of another protein for example through a protein-protein interaction. Another way the embryo repressor may work is to deter or prevent the expression of the embryo lethality polynucleotide, for example by expressing a molecule that binds to the promoter of the lethality polynucleotide and blocks some or all expression. Another example that could be used in the system is gene silencing. For example, the embryo repressor may be a polynucleotide that prevents the embryo lethal polynucleotide from functioning through gene silencing.

The embryo lethality polynucleotide and the embryo lethality repressor polynucleotide are not limited to being expressed only in the embryo. The genes can be expressed in other tissues. It is more effective if the embryo lethality polynucleotide is not expressed in the endosperm so that the haploid seed can develop normally. Another consideration for the method to work at its optimum is that the embryo lethality polynucleotide expression should to be matched by the expression of the embryo lethality repressor polynucleotide. Anytime the polynucleotides are inherited together the embryo lethality repressor polynucleotide should be expressed at a level to deter the negative effects of the embryo lethality polynucleotide.

Typically, the non-transmission pollen polynucleotide and the embryo lethality repressor are linked in the developed inducer line. They may be tightly linked. For the most convenience the non-transmission pollen polynucleotide and the embryo lethality repressor should be adjacent to each other, for example on the same construct. For efficient results the non-transmission pollen polynucleotide and the embryo lethality repressor will segregate together. Also typically the non-transmission pollen polynucleotide and the lethality repressor are linked, but are at a different location than the embryo lethality polynucleotide. For efficient results, the embryo lethality polynucleotide will segregate from the non-transmission pollen polynucleotide and the embryo lethality repressor. For the greatest efficiency, the embryo lethality polynucleotide is not linked to the non-transmission pollen polynucleotide and the embryo lethality repressor.

The developed inducer line may or may not contain selectable markers. It may or may not be developed using transgenes that are selectable markers.

The following describes typical components for producing an inducer line. Construct A, comprises a non-transmission pollen polynucleotide and an embryo lethality repressor, and a selectable marker gene. Construct B comprises a selectable marker gene and an embryo lethality gene. To facilitate segregation upon pollination the two constructs can be located at two different locations in the genome. For further efficiency Construct A and Construct B should be unlinked.

Construct A and B can be co-transformed into the inducer line or the transformation process can be done sequentially, most conveniently with Construct A first and Construct B second. The initial $T_0$ inducer plant will be heterozygous for both constructs, A and B. The expected results of the self-pollination of this plant are given in Table 1.

Another way to introduce the constructs into the inducer line would be to cross or breed them into the inducer line. For example, Construct A and Construct B could be co-transformed into a plant and then bred into an inducer line. For the system to be the most efficient in plants, the embryo lethal repressor needs to present with the embryo lethal polynucleotide. Therefore, one may transform with construct containing the embryo lethal repressor polynucleotide to obtain stably transformed cells and then transform with construct comprising the embryo lethal polynucleotide.

TABLE 1

Self-pollination of a $T_0$ plant co-transformed at 2 segregating loci (genotype (A-B-). $T_0$ plant production is possible because both the embryo lethal and the embryo lethal repressor are both expressed in somatic embryos and embryogenic callus. Pollen containing Construct A is non-viable or non-transmissible. Embryos containing Construct B but not Construct A are non-viable due to the expression of the embryo lethal gene without the embryo lethal repressor gene. The A-BB genotype will have two doses of the embryo lethal gene and one dose of the embryo repressor gene. Therefore for the greatest efficiency, the expression of a single repressor polynucleotide should be at a level that will prevent lethality of two doses of the embryo lethal polynucleotide.

| | | Male Gametes | | | |
|---|---|---|---|---|---|
| | | AB | A- | -B | -- |
| Female Gametes | AB | non-transmission of pollen | non-transmission of pollen | A-BB Viable embryo | A-B- Viable embryo |
| | A- | non-transmission of pollen | non-transmission of pollen | A-B- Viable embryo | A--- Viable embryo but sensitive to selectable marker agent b |
| | -B | non-transmission of pollen | non-transmission of pollen | --BB Embryo lethal | --B- Embryo lethal |
| | -- | non-transmission pollen | non-transmission pollen | --B- Embryo lethal | ---- Embryo viable but sensitive to selectable marker (a and b) agents |

Construct A = non-transmission pollen + embryo lethal repressor + selectable marker gene "a"
Construct B = embryo lethal + selectable marker "b"

Because there will be viable embryos without both constructs, the embryos or plants from embryos not containing both constructs can be selected against by contacting the tissue with the selectable agent. If the selectable marker is a visual marker, or some other type of marker, this can also be observed and the tissue not containing both markers can be selected against. Any type of selectable markers can be used. The remaining plants will either be heterozygous for both constructs (A-B-) or heterozygous for construct A and homozygous for construct B, (A-BB). The result of selfing the A-B-genotype will result in the progeny as seen previously, Table 1. The result of selfing the A-BB genotype will give you only genotypes with that are homozygous for Construct B. Therefore all the progeny will have the selectable marker b. This is the desired genotype, A-BB. The plants that are heterozygous for both constructs will produce some progeny that do not contain selectable marker b. The resultant progeny from selfing the A-BB genotypes are described in Table 2.

TABLE 2

Self-pollination of $T_1$ plants having A-BB genotype. All viable progeny from selfed A-BB plants will be A-BB plants.

|  |  | Male Gametes | |
| --- | --- | --- | --- |
|  |  | AB | -B |
| Female Gametes | AB | non-transmission of pollen | A-BB Viable embryo |
|  | -B | non-transmission of pollen | --BB Embryo lethal |

The desired genotype, A-BB, produces only one viable pollen genotype, -B. When this transgenic inducer line is crossed as a male to a wildtype female, this will result in the ablation of all diploid embryos, Table 3. However maternal haploid embryos do not inherit the embryo lethal from the male parent and are therefore viable. The maternal haploids do not contain the transgenes from Construct A or Construct B.

Even though the maternal haploid embryo does not inherit the DNA from the male parent, the pollen carrying the embryo lethal gene will have one sperm nucleus that fuses with the polar nuclei in the embryo sac to create a triploid (3N) endosperm. Therefore the embryo lethal gene either cannot be expressed in the endosperm or aleurone; or if it is expressed in these cells it will not kill the haploid embryo.

TABLE 3

Cross of the haploid-induction line, with genotype A-BB, to a wildtype female line, ----. Pollen containing Construct A and embryos containing Construct B are nonviable due to the expression of the embryo lethal without the expression of the embryo lethal repressor. Diploids inherit Construct B from the male and are nonviable. Maternal haploids do not inherit Construct B and are viable. Any maternal embryos that develop normally will be haploid.

|  |  | Male Gametes (inducer line) | | |
| --- | --- | --- | --- | --- |
|  |  | AB | -B | No male contribution |
| Female Gametes (wildtype) | -- | non-transmission of pollen | Embryo lethal | Maternal haploid |

The development of an inducer line could also be produced without any selectable markers. It could also be produced using only one selectable marker on either construct or with the same selectable marker on both constructs. One could use any number of techniques known to one of skill in the art to track and breed for the transgenes. For example progeny tests, PCR, molecular markers, or ELISA could be used to track the transgenes. Also any combination of techniques could be used. For example if a first construct=pollen non-transmission+embryo lethal repressor and a second construct=embryo lethal, quantitative PCR could be used to determine which progeny contain which construct and in what dose, homozygous state or heterozygous state.

Another method of the invention includes co-transformation with the pollen non-transmission and embryo lethal repressor genes on one construct and a selectable marker gene on a second construct. After obtaining transformed tissue a second co-transformation can be conducted with the embryo lethal and a second selectable marker. After transgenic plants are developed the selectable markers can be segregated away from the other transgenes.

Another method may be utilized with chemical application or contact acting as the embryo lethal repressor One may be able to obtain plants with only Construct B if a chemical can be used to repress the embryo lethal polynucleotide. For example, one could transform the constructs into two different plants and then breed both constructs into the inducer line. The chemical that represses the embryo lethality would have to be used for the plant transformed with Construct B until the both constructs are contained in the same plant. One would then select for an inducer line containing the two segregating constructs, A and B. Trait integration through backcrossing is well known in the art.

Haploid induction systems have been developed for various plants to produce haploid tissues, plants and seeds. The haploid induction system can produce haploid plants from any genotype by crossing a selected line (as female) with an inducer line. Such inducer lines for maize include, but are not limited to, Stock 6 and Stock 6 derivatives (Coe, 1959, Am. Nat. 93:381-382; Sarkar and Coe, 1966, Genetics 54:453-464; Sarkar et al, 1972, Development of maternal-haploidy-inducer lines in maize (Zea mays L.) Indian J. Agric. Sci. 42:781-786; Lashermes and Beckert, 1988, Genetic control of maternal haploidy in maize (Zea mays L.) and selection of haploid inducing lines. Theor. Appl. Genet. 76:405-410; Chalyk, S. T. 1994, Properties of maternal haploid maize plants and potential application to maize breeding. Euphytica 79; 13-18; Bordes, J. R. et al., 1997, Haploidization of maize (Zea mays L.) through induced gynogenesis assisted by glossy markers and its use in breeding. Agronomie 17:291-297; Eder J. and S. Chalyk, 2002, In vivo haploid induction in maize. Theor. Appl. Genet. 104:703-708) RWS (Rober, Gordillo, and Geiger, 2005, Maydica 50 (2005) 275-283), KEMS (Deimling, Roeber, and Geiger, 1997, Vortr. Pflanzenzuchtg 38:203-224), or KMS and ZMS (Chalyk, Bylich & Chebotar, 1994, MNL 68:47; Chalyk & Chebotar, 2000, Plant Breeding 119:363-364), and indeterminate gametophyte (ig) mutation (Kermicle 1969 Science 166:1422-1424). The disclosures of which are incorporated herein by reference.

Wide hybridization crosses can also be used to produce haploids. In barley, this method is sometimes referred to as the bulbosum method (Kasha and Kao, 1970, Nature 225: 874-876). This method of haploid production occurs due to the elimination of the chromosomes from the pollinating parent.

When an inducer line is used to pollinate a diploid plant, haploid embryos are derived. One sperm nucleus from the pollen fuses with the polar nuclei in the embryo sac to create a triploid (3N) endosperm. The triploid endosperm will contain 2 sets of chromosomes from the female and 1 set of chromosomes from the male, which in this case is the inducer line. The haploid embryo contains a single set of chromosomes, which are derived from the female plant.

In the development of haploid maize, Rnj is a commonly used allele for haploid/diploid screening of mature seeds (Nanda and Chase, 1966. An embryo marker for detecting monoploids of maize (Zea mays L). Crop Sci. 6:213-215; Greenblatt and Bock, 1967. A commercially desirable procedure for detection of monoploids in maize. J. Hered. 58:9-13).

R-nj expression levels have been shown to be correlated with parameters of kernel maturation (Alexander and Cross, 1983, Grain fill characteristics of early maize (*Zea mays* L) strains selected for variable R-nj expression, Euphytica 32:839-844.). More recently, R-scm2 has also been used (Kato A., 2002, Chromosome doubling of haploid maize seedlings using nitrous oxide gas at the flower primordial stage. Plant breeding 121:370-377; and Kato A., 2003, Chromosome doubling method, U.S. Publication 2003/0005479).

The R-nj anthocyanin marker gene used to distinguish haploids and diploids at the mature seed stage is not expressed until late in embryo development. To identify haploid tissue at an earlier stage, haploid embryos can be identified using a transgenic marker, lec1-GFP, which is present in the inducer line. The use of lec1-GFP is valuable because the gene allows one to identify the non-haploid embryos at an early stage of embryo development (U.S. application Ser. No. 09/718,754, U.S. Pat. No. 6,486,382). The absence of the GFP marker expression is used to identify haploid embryos. Although the haploid embryos can be identified at an early stage, the GFP system requires a labor intensive screening process to determine which embryos express the GFP marker and which embryos do not express the GFP marker. The use of a lethal marker in an inducer line would only allow haploid embryo formation and thus eliminate the need for a less efficient screening process. This system would increase the efficiency of the doubled haploid process.

Various types of systems could be utilized in the inducer line in order to increase the efficiency of the doubled haploid process: 1) toxicity/antidote systems 2) transcriptional regulator systems 3) gene silencing systems.

An example of an toxicity/antidote system that can be utilized is the Barnase/Barstar system. Barnase is the name of the extracellular ribonuclease produced by *Bacillus amyloliquefaciens*. The inhibitor of barnase is called barstar and is produced intracellularly by the same organism that secretes barnase. The function of barstar is to protect the *B. amyloliquefaciens* from the toxic effects of intracellular barnase, rendering it inactive (Hartley, R. W. (1989) Barnase and barstar: Two small proteins to fit and fold together. Trends Biochem. Sci. 14:450-454). Both of these genes have been cloned and sequenced (Hartley, R. W. (1988) Barnase and barstar: Expression of its cloned inhibitor permits expression of a cloned ribonuclease. J. Mol. Biol. 202:913-915). It has been shown that barnase expression is lethal to plant cells, and that barstar can protect a plant cell from the effects of barnase (Mariani et al., (1990) Induction of male-sterility in plants by a chimeric ribonuclease gene. Nature 347:737-741; Mariani et al. (1992) A chimeric ribonuclease-inhibitor gene restores fertility to male sterile plants. Nature 357:384-387; Beals, T. P. and Goldberg, R. B. (1997) A novel cell ablation strategy blocks tobacco anther dehiscence. Plant Cell 9:1527-1545; Williams et al., (1997) Male sterility through recombinant DNA technology. In Pollen Biotechnology for Crop Production and Improvement, K. R. Shivanna and V. K. Sawhney, eds (Cambridge, UK: Cambridge University Press) pp 237-257). The transmission of a transgene through pollen can be prevented by linking the transgene to a pollen-lethality gene composed of a cytotoxic gene under the control of a pollen-specific (gametophyte) promoter (Twell (1995) Diptheria toxin-mediated cell ablation in developing pollen: vegetative cell ablation blocks generative cell migration. Protoplasma 187:144-154; Williams et al., (1997) Male sterility through recombinant DNA technology. In Pollen Biotechnology for Crop Production and Improvement, K. R. Shivanna and V. K. Sawhney, eds (Cambridge, UK: Cambridge University Press) pp 237-257). This type of construct can be maintained because it is transmitted through the female. Many pollen specific promoters have been identified. Other embodiments of the invention include constructs that would deter anther viability or any construct that would prevent viable pollen transmission. Barstar inhibits the function (RNase) of the barnase protein in the haploid-inducer line. Diploid embryos are ablated because the barstar PTU (plant transcription unit) is linked to the pollen non-transmission PTU, and thus is not present in the diploid embryos to inhibit barnase. The barstar system can be improved by optimizing the coding region of the barstar gene. One may also optimize the system by increasing the affinity of barstar to barnase. Other ways of improving the system include increasing the expression of barstar over the expression level of barnase so that the expression level is, for example about 1.5×, 2×, or at least 3× the level of the expression of barnase. One may have barnase regulated by an embryo preferred promoter, for example led, and have barstar regulated by a constitutive promoter, for example Ubi. One may also add introns, such as Adh introns, or add enhancers, such as 35S enhancers in order to increase expression. Introns may be needed in the polynucleotide that expresses a toxic product for the purpose of preventing expression of the toxic product in the *Agrobacterium*.

There are many examples of transcriptional regulator systems that can be utilized (Ramos et al. "The tetr family of transcriptional repressors" (2005) Microbiology and Molecular Biology Reviews, vol. 69(2): 326-356). Some examples of regulator families are indicated in Table 4.

TABLE 4

Regulator Families

| Family | Action | Examples of regulated functions | DNA binding motif | Position |
| --- | --- | --- | --- | --- |
| LysR | Activator/repressor | Carbon and nitrogen metabolism | Helix-turn-helix | N-terminal |
| AraC/XylS | Activator | Carbon metabolism, stress response and pathogenesis | Helix-turn-helix | C-terminal |
| TetR | Repressor | Biosynthesis of antibiotics, efflux pumps, osmotic stress, etc. | Helix-turn-helix | C-terminal |
| LuxR | Activator | Quorum sensing, biosysnthesis and metabolism, etc. | Helix-turn-helix | C-terminal |
| LacI | Repressor | Carbon source utilization | Helix-turn-helix | N-terminal |
| ArsR | Repressor | Metal resistance | Helix-turn-helix | Central |

TABLE 4-continued

Regulator Families

| Family | Action | Examples of regulated functions | DNA binding motif | Position |
|---|---|---|---|---|
| IclR | Repressor/ activator | Carbon metabolism, efflux pumps | Helix-turn-helix | N-terminal |
| MerR | Repressor | Resistance and detoxification | Helix-turn-helix | N-terminal |
| AsnC | Activator/ repressor | Amino acid biosynthesis | Helix-turn-helix | N-terminal |
| MarR | Activator/ repressor | Multiple antibiotic resistance | Helix-turn-helix | Central |
| NtrC (EBP) | Activator | Nitrogen assimilation, aromatic amino acid synthesis, flagella, catabolic pathways, phage response etc. | Helix-turn-helix | C-terminal |
| OmpR | Activator | Heavy metal and virulence | Winged helix | C-terminal |
| DeoR | Repressor | Sugar metabolism | Helix-turn-helix | N-terminal |
| Cold shock | Activator | Low-temperature resistance | RNA binding domain (CSD) | Variable |
| GntR | Repressor | General metabolism | Helix-turn-helix | N-terminal |
| Crp | Activator/ repressor | Global responses, catabolic repression and anaerobiosis | Helix-turn-helix | C-terminal |

A well studied regulator system that can be utilized to identify haploids early in development is the tet repressor system. The tetracycline operon system, comprises repressor and operator elements. The operon system is controlled by the presence of tetracycline, and self-regulates the level of expression of tetA and tetR genes. The product of tetA removes tetracycline from the cell. The product of tetR is the repressor protein which binds to the operator elements with a $K_d$ of about 10 pM in the absence of tetracycline, thereby blocking expression or tetA and tetR. The TET repressor can be optimized for maize and the promoter used to stop development of the embryo can be modified with TET operator sequences.

Another example of a system that can be utilized to identify haploids early in development utilizes the lac repressor system (Ulmasov et al. (1997) Plant Mol Biol 35-417-424; Wilde et al. (1992) EMBO J 11:1251-1259). This repressor/operator based-system is derived from the prokaryotic operon, E. coli lactose operon. This system controls the activity of a promoter by placing operator sequences near the transcriptional start site of a gene such that gene expression from the operon is inhibited upon the binding of the repressor protein to its cognate operator sequence. However, in the presence of an inducing agent, the binding of the repressor to its operator is inhibited, thus activating the promoter and enabling gene expression. In the lac system, isopropyl-B-D-thiogalactopyranoside (IPTG) is the commonly used inducing agent, while tetracycline, and/or doxycyline are commonly used inducing agents for the tet system. The lac repressor has been extensively characterized. The lac repressor has a high association constant for its operator, and IPTG reduces the affinity of repressor for the operator by 300-fold (Barkley & Bourgeois (1980) The Operon, Miller & Reznikoff, Eds., Cold Spring Harbor Press, Cold Spring Harbor, N.Y., pp 177-220), only 30-fold repression has been reported using the lactose repressor (Ulmasov et al. (1997) Plant Mol Biol 35-417-424). The lac repressor can be maize optimized and the promoter used to stop development of the embryo can be modified with lac operator sequences.

Gene silencing may also be used in the selective ablation of diploid embryos system. The repression of embryo lethality may be at the RNA or protein stage for example, anti-sense RNA, hair-pins, and other mechanisms for gene silencing. For example one could have the barnase hairpin polynucleotide driven by a strong promoter such as UBI. This construct comprising the hairpin can be linked to a construct that does not allow pollen fertilization. The other construct could comprise the barnase polynucleotide driven by the led promoter. This would effectively turn off barnase until the hairpin locus was segregated away. Any polynucleotide that prevents normal development of the embryo along with a corresponding gene silencing construct can be used in the system.

Examples of genes that may be driven by a pollen promoter and used to prevent fertile pollen in the invention include DAM (GenBank J01600, Nucleic Acids Res. 11:837-851 (1983); alpha-amylase (GenBank L25805, Plant Physiol. 105 (2):759-760 (1994)); D8 (Physiol. Plant 100(3):550-560 (1997)); SacB (Plant Physiol. 110(2):355-363 (1996)), lipases and ribonucleases; tasselseed2 (ts2) (Calderon-Urrea M. and S. L. Dellaporta (1999) Development 126:435-441); diphtheria toxin A (DTA) (Greenfield et al. Proc. Natl. Acad. Sci. 80:6853 (1983); Palmiter et al., Cell 50:435 (1987)).

Examples of pollen specific promoters that can be used include but are not limited to PG47 (Rogers et al. (1991), Pollen specific cDNA clones from Zea mays, Biochem. Biophys. Acta 1089, 411-413; Allen, R. L., and Lonsdale, D. M. (1992) Sequence analysis of three members of the maize polygalacturonase gene family expressed during pollen development, Plant Mol. Biol. 20, 343-345, Allen, R. L., and Lonsdale, D. M. (1993), Molecular characterization of one of the maize polygalacturonase gene family members which are expressed during late pollen development. The Plant Journal 3, 261-271, U.S. Pat. No. 5,412,085 and U.S. Pat. No. 5,545, 546); maize pollen-specific gene Zm13 (Hamilton et al. (1992) Plant Mol. Biol. 18:211-218; Guerrero et al. (1993) Mol. Gen. Genet. 224:161-168); microspore-specific promoters such as the apg gene promoter (Twell et al., Sex. Plant Reprod. 6:217-224 (1993)); further include a sunflower pollen-expressed gene SF3 (Baltz et al. (1992) The Plant Journal 2:713-721), B. napus pollen specific genes (Arnoldo et al. (1992) J. Cell. Biochem, Abstract No. Y101204). Such promoters are known in the art or can be discovered by known techniques; see, e.g., Bhalla and Singh (1999) Molecular control of male fertility in Brassica Proc. 10$^{th}$ Annual Rapeseed Congress, Canberra, Australia; van Tunen et al. (1990) Pollen-specific chi promoters from petunia: tandem promoter regulation of the chiA gene, Plant Cell 2:393-40; Jeon et al. (1999); and Twell et al. (1993) Activation and developmental regulation of an *Arabidopsis* anther-specific promoter in microspores and pollen of *Nicotiana tabacum*, Sex. Plant Reprod. 6:217-224.

Many examples of pollen promoters and the polynucleotides used with them to prevent viable pollen can be found in U.S. Pat. No. 6,743,968 and US Publication 2005/0246796 (U.S. application Ser. No. 11/014,071).

Cereal genes whose promoters are associated with early seed and embryo development include lec1 (U.S. Pat. No. 7,122,658), rice glutelin ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice prolamin (Zhou & Fan, 1993, Transgenic Res 2:141-6), wheat prolamin (Hammond-Kosack et al., 1993, EMBO J 12:545-54), maize zein (Z4, Matzke et al., 1990, Plant Mol Biol 14:323-32), and barley *B-hordeiis* (Entwistle et al., 1991, Plant Mol Biol 17:1217-31). "Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108. Such seed-preferred promoters include, but are not limited to, Cim1 (cytokinin-induced message), cZ19B1 (maize 19 kDa zein), milps (myo-inositol-1-phosphate synthase); see WO 00/11177 and U.S. Pat. No. 6,225,529. Gamma-zein is an endosperm-specific promoter. Globulin-1 (Glob-1) is a representative embryo-specific promoter. The maize Glb1 gene encodes globulin-1, a major embryo storage protein. (Kriz, A. L., et al. (1986) Plant Physiol. 82:1069-1075) Glb1 is expressed in the developing maize seed during embryo development. (Belanger, F. C., et al. (1989) Plant Physiol. 91:636-643) The promoter region of Glb1 has been identified, cloned, and introduced into tobacco plants by *Agrobacterium*-mediated transformation. (Liu, S., et al. (1996) Plant Cell Reports 16:158-162) The transformed plants demonstrate that the Glb1 promoter has desirable temporal and tissue specificity. The Glb1 promoter is positively regulated by abscisic acid (ABA). (Kriz, A. L., et al. (1990) Plant Physiol. 92:538-542; Paiva, R., et al., (1994) Planta 192:332-339) Levels of the plant hormone ABA are known to fluctuate under conditions of cold or desiccation. (Himmelbach, A., et al. (1998) Phil. Trans. R. Soc. Lond. 353:1439-1444) Thus, the activity of the Glb1 promoter can be differentially affected. From dicots, seed-specific promoters include, but are not limited to, bean β-phaseolin, napin, β-conglycinin, soybean lectin, cruciferin, and the like. More examples of seed-specific promoters from monocots include, but are not limited to, maize 15 kDa zein; 22 kDa zein; 27 kDa zein (Boronat, A., Martinez, M. C., Reina, M., Puigdomenech, P. and Palau, Jr.; Isolation and sequencing of a 28 kD glutelin-2 gene from maize: Common elements in the 5' flanking regions among zein and glutelin genes; *Plant Sci.* 47:95-102 (1986)); gamma-zein; waxy (Kloesgen, R. B., Gierl, A., Schwarz-Sommer, Z. S. and Saedler, H., Molecular analysis of the waxy locus of *Zea mays, Mol. Gen. Genet.* 203:237-244 (1986)); shrunken 1; shrunken 2 (Shaw et al., Plant Phys 98:1214-1216, 1992; Zhong Chen et al., PNAS USA 100:3525-3530, 2003); globulin 1; mZE40-2, also known as Zm-40, U.S. Pat. No. 6,403,862; an ltp2 promoter (Kalla, et al., Plant Journal 6:849-860 (1994); U.S. Pat. No. 5,525,716), cim1 promoter (see U.S. Pat. No. 6,225,529); nuc1c (U.S. Pat. No. 6,407,315); etc. See also WO 00/12733 and U.S. Pat. No. 6,528,704, where seed-preferred promoters from end1 and end2 genes are disclosed. Additional embryo specific promoters are disclosed in Sato et al. (1996) *Proc. Natl. Acad. Sci.* 93:8117-8122 (rice homeobox, OSH1); and Postma-Haarsma et al. (1999) *Plant Mol. Biol.* 39:257-71 (rice KNOX genes). Additional endosperm specific promoters are disclosed in Albani et al. (1984) *EMBO* 3:1405-15; Albani et al. (1999) *Theor. Appl. Gen.* 98:1253-62; Albani et al. (1993) *Plant J.* 4:343-55; Mena et al. (1998) *The Plant Journal* 116:53-62 (barley DOF); Opsahl-Ferstad et al. (1997) *Plant J* 12:235-46 (maize Esr); and Wu et al. (1998) *Plant Cell Physiology* 39:885-889 (rice GluA-3, GluB-1, NRP33, RAG-1).

Examples of constitutive promoters include the 1'- or 2'-promoter of *Agrobacterium tumefaciens* (see, e.g., O'Grady (1995) *Plant Mol. Biol.* 29:99-108). Other plant promoters include the ribulose-1,3-bisphosphate carboxylase small subunit promoter, the phaseolin promoter, alcohol dehydrogenase (Adh) gene promoters (see, e.g., Millar (1996) *Plant Mol. Biol.* 31:897-904), sucrose synthase promoters, α-tubulin promoters, actin promoters, such as the *Arabidopsis* actin gene promoter (see, e.g., Huang (1997) *Plant Mol. Biol.* 1997 33:125-139), cab, PEPCase, R gene complex, ACT11 from *Arabidopsis* (Huang et al. *Plant Mol. Biol.* 33:125-139 (1996)), Cat3 from *Arabidopsis* (Zhong et al., *Mol. Gen. Genet.* 251:196-203 (1996)), the gene encoding stearoyl-acyl carrier protein desaturase from *Brassica napes* (Solocombe et al. (1994) *Plant Physiol.* 104:1167-1176), GPc1 from maize (Martinez et al. (1989) *J. Mol. Biol* 208: 551-565), Gpc2 from maize (Manjunath et al. (1997), *Plant Mol. Biol.* 33:97-112), and other transcription initiation regions from various plant genes known to those of skill. See also Holtorf (1995) *"Comparison of different constitutive and inducible promoters for the overexpression of transgenes in Arabidopsis thaliana," Plant Mol. Biol.* 29:637-646. The promoter sequence from the E8 gene (see, Deikman and Fischer (1988) *EMBO J* 7:3315) and other genes can also be used, along with promoters specific for monocotyledonous species (e.g., McElroy D., et al. (1994.) *Foreign gene expression in transgenic cereals, Trends Biotech.* 12:62-68). Other constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Yet, other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

In addition to the promoters noted herein, promoters of bacterial origin which operate in plants can be used in the invention. They include, e.g., the octopine synthase promoter, the nopaline synthase promoter and other promoters derived from Ti plasmids. See, Herrera-Estrella et al. (1983) *Nature* 303:209. Viral promoters can also be used. Examples of viral promoters include the 35S and 19S RNA promoters of cauliflower mosaic virus (CaMV). See, Odell et al., (1985) *Nature* 313:810; and, Dagless (1997) *Arch. Virol.* 142:183-191. Other examples of constitutive promoters from viruses which infect plants include the promoter of the tobacco mosaic virus; cauliflower mosaic virus (CaMV) 19S and 35S promoters or the promoter of Figwort mosaic virus, e.g., the figwort mosaic virus 35S promoter (see, e.g., Maiti (1997) *Transgenic Res.* 6:143-156), etc. Alternatively, novel promoters with useful characteristics can be identified from any viral, bacterial, or plant source by methods, including sequence analysis, enhancer or promoter trapping, and the like, known in the art.

Tissue-preferred (tissue-specific) promoters and enhancers can be utilized to target enhanced gene expression within a particular plant tissue. Tissue-preferred (tissue-specific) promoters include, e.g., those described in Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) Plant Physiol. 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weaker expression or stronger expression. A tissue-specific promoter can drive expression of operably linked sequences in tissues other than the target tissue. Thus, as used herein, a tissue-specific promoter is one that drives expression preferentially in the target tissue, but can also lead to some expression in other tissues as well.

In certain embodiments, leaf specific promoters can be used, e.g., pyruvate, orthophosphate dikinase (PPDK) promoter from C4 plant (maize), cab-m1 Ca+2 promoter from maize, the *Arabidopsis thaliana* myb-related gene promoter (Atmyb5), the ribulose biphosphate carboxylase (RBCS) promoters (e.g., the tomato RBCS1, RBCS2 and RBCS3A genes, which are expressed in leaves and light-grown seedlings, while RBCS1 and RBCS2 are expressed in developing tomato fruits, and/or a ribulose bisphosphate carboxylase promoter which is expressed almost exclusively in mesophyll cells in leaf blades and leaf sheaths at high levels, etc.), and the like. See, e.g., Matsuoka et al., (1993) *Tissue-specific light-regulated expression directed by the promoter of a C4 gene, maize pyruvate, orthophosphate dikinase, in a C3 plant, rice*, PNAS USA 90(20):9586-90; (2000) *Plant Cell Physiol.* 41(1):42-48; (2001) *Plant Mol. Biol.* 45(1):1-15; Shiina, T. et al., (1997) *Identification of Promoter Elements involved in the cytosolic Ca+2 mediated photoregulation of maize cab-m1 expression*, Plant Physiol. 115:477-483; Casal (1998) *Plant Physiol.* 116:1533-1538; Li (1996) FEBS Lett. 379:117-121; Busk (1997) *Plant J.* 11:1285-1295; and, Meier (1997) *FEBS Lett.* 415:91-95; and, Matsuoka (1994) *Plant J.* 6:311-319. Other leaf-specific promoters include, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

In certain embodiments, senescence specific promoters can be used (e.g., a tomato promoter active during fruit ripening, senescence and abscission of leaves, a maize promoter of gene encoding a cysteine protease, and the like). See, e.g., Blume (1997) *Plant J.* 12:731-746; Griffiths et al., (1997) *Sequencing, expression pattern and RFLP mapping of a senescence-enhanced cDNA from Zea Mays with high homology to oryzain gamma and aleurain*, Plant Mol. Biol. 34(5):815-21; *Zea mays* partial see1 gene for cysteine protease, promoter region and 5' coding region, Genbank AJ494982; Kleber-Janke, T. and Krupinska, K. (1997) *Isolation of cDNA clones for genes showing enhanced expression in barley leaves during dark-induced senescence as well as during senescence under field conditions*, Planta 203(3):332-40; and, Lee, R H et al., (2001) *Leaf senescence in rice plants: cloning and characterization of senescence up-regulated genes*, J. Exp. Bot. 52(358):1117-21.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue (see, e.g., *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also, U.S. Pat. Nos. 5,837,876; 5,750,386; 5,633,363; 5,459,252; 5,401,836; 5,110,732; and 5,023,179.

The use of temporally-acting promoters is also contemplated by this invention. For example, promoters that act from 0-25 days after pollination (DAP), 4-21, 4-12, or 8-12 DAP can be selected, e.g., promoters such as cim1 and ltp2. Promoters that act from 0-14 days after pollination can also be used, such as SAG12 (See WO 96/29858, Richard M. Amasino, published 3 Oct. 1996) and ZAG1 or ZAG2 (See R. J. Schmidt, et al., *Identification and Molecular Characterization of ZAG1, the Maize Homolog of the Arabidopsis Floral Homeotic Gene AGAMOUS*, Plant-Cell 5(7):729-37 (July 1993)). Other useful promoters include maize zag2. 1, Zap (also known as ZmMADS; U.S. patent application Ser. No. 10/387,937; WO 03/078590); and the maize tb1 promoter (see also Hubbarda et al., Genetics 162:1927-1935, 2002).

Shoot-preferred promoters include, shoot meristem-preferred promoters such as promoters disclosed in Weigel et al. (1992) *Cell* 69:853-859; Accession No. AJ131822; Accession No. Z71981; Accession No. AF059870, the ZAP promoter (U.S. patent application Ser. No. 10/387,937), the maize promoter (Wang et al. (1999) *Nature* 398:236-239, and shoot-preferred promoters disclosed in McAvoy et al. (2003) *Acta Hort.* (*ISHS*) 625:379-385.

An inducible promoter is a promoter that is capable of directly or indirectly activating transcription of one or more DNA sequences or genes in response to an inducer. In the absence of an inducer, the DNA sequences or genes will not be transcribed, or will be transcribed at a level lower than in an induced state. The inducer can be a chemical agent, such as a metabolite, growth regulator, herbicide or phenolic compound, or a physiological stress directly imposed upon the plant such as cold, drought, heat, salt, toxins. Plant promoters which are inducible upon exposure to plant hormones, such as auxins, can be used. For example, the invention can use the auxin-response elements E1 promoter subsequence (AuxREs) from the soybean (*Glycine max* L.) (Liu (1997) Plant Physiol. 115:397-407); the auxin-responsive *Arabidopsis* GST6 promoter (also responsive to salicylic acid and hydrogen peroxide) (Chen (1996) Plant J. 10:955-966); the auxin-inducible parC promoter from tobacco; a plant biotin response element (Streit (1997) Mol. Plant Microbe Interact. 10:933-937); and the promoter responsive to the stress hormone abscisic acid (Sheen (1996) Science 274:1900-1902). Plant promoters which are inducible upon exposure to chemical reagents which can be applied to the plant, such as herbicides or antibiotics, are also used to express polynucleotides. The promoter can be a chemical-inducible promoter, where application of the chemical induces gene expression, or a chemical-repressible promoter, where application of the chemical represses gene expression. For example, the maize In2-2 promoter, activated by benzenesulfonamide herbicide safeners, can be used (De Veylder (1997) Plant Cell Physiol. 38:568-577); application of different herbicide safeners induces distinct gene expression patterns, including expression in the root, hydathodes, and the shoot apical meristem. An ACC synthase coding sequence or RNA configuration can also be under the control of, e.g., tetracycline-inducible and tetracycline-repressible promoters (see, e.g., Gatz et al. (1991) Mol. Gen. Genet. 227:229-237; U.S. Pat. Nos. 5,814, 618 and 5,789,156; and, Masgrau (1997) Plant J. 11:465-473 (describing transgenic tobacco plants containing the *Avena sativa* L. (oat) arginine decarboxylase gene with a tetracycline-inducible promoter); or, a salicylic acid-responsive element (Stange (1997) Plant J. 11:1315-1324. Other chemical-inducible promoters are known in the art and include, but are not limited to, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) Proc. Natl. Acad. Sci. USA 88:10421-10425 and McNellis et al. (1998) Plant J. 14(2):247-257).

Examples of inducible regulatory elements include a metallothionein regulatory element, a copper-inducible regulatory element, or a tetracycline-inducible regulatory element, the transcription from which can be effected in response to divalent metal ions, copper or tetracycline, respectively (Furst et al., Cell 55:705-717, 1988; Mett et al., Proc. Natl. Acad. Sci., USA 90:4567-4571, 1993; Gatz et al., Plant J. 2:397-404, 1992; Roder et al., Mol. Gen. Genet. 243:32-38, 1994). Inducible regulatory elements also include an ecdysone regulatory element or a glucocorticoid regulatory element, the transcription from which can be effected in response to ecdysone or other steroid (Christopherson et al., Proc. Natl. Acad. Sci., USA 89:6314-6318, 1992; Schena et al., Proc. Natl. Acad. Sci., USA 88:10421-10425, 1991; U.S. Pat. No. 6,504, 082); a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al. (1997) Plant J. 12(2):255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene which responds to benzenesulfonamide herbicide safeners (Hershey et al., Mol. Gen. Gene 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as P5CS (Zang et al. (1997) Plant Sciences 129:81-89); cold-inducible promoters, such as, cor15a (Hajela et al. (1990) Plant Physiol. 93:1246-1252), cor15b (Wlihelm et al. (1993) Plant Mol Biol 23:1073-1077), wsc120 (Ouellet et al. (1998) FEBS Lett. 423-324-328), ci7 (Kirch et al. (1997) Plant Mol Biol. 33:897-909), ci21A (Schneider et al. (1997) Plant Physiol. 113:335-45); drought-inducible promoters, such as, Trg-31 (Chaudhary et al. (1996) Plant Mol. Biol. 30:1247-57), rd29 (Kasuga et al. (1999) Nature Biotechnology 18:287-291); osmotic inducible promoters, such as Rab17 (Vilardell et al. (1991) Plant Mol. Biol. 17:985-93) and osmotin (Raghothama et al. (1993) Plant Mol Biol 23:1117-28); and heat inducible promoters, such as heat shock proteins (Barros et al. (1992) Plant Mol. 19:665-75; Marrs et al. (1993) Dev. Genet. 14:2741), smHSP (Waters et al. (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al. (1993) Mol. Gen. Genetics 236:331-340). Certain promoters are inducible by wounding, including the *Agrobacterium* pmas promoter (Guevara-Garcia et al. (1993) Plant J. 4(3):495-505) and the *Agrobacterium* ORF13 promoter (Hansen et al., (1997) Mol. Gen. Genet. 254(3):337-343).

The expression cassette used in the invention can include, at the 3' terminus of the heterologous nucleotide sequence of interest, a transcriptional and translational termination region functional in plants. The termination region can be native with the promoter nucleotide sequence of the present invention, can be native with the DNA sequence of interest, or can be derived from another source. Convenient termination regions are available from the Ti-plasmid of *A. tumefaciens*, such as the octopine synthase and nopaline synthase termination regions. The 3' terminus of the pinII—(potato proteinase inhibitor) can be used. See Ryan (1990) *Ann. Rev. Phytopath.* 28:425-449; Duan et al. (1996) Nature Biotechnology 14:494-498. For other 3' terminus sequences see also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. 1989) *Nucleic Acids Res.* 17:7891-7903; Joshi et al. (1987) *Nucleic Acid Res.* 15:9627-9639.

The expression cassettes can additionally contain 5' leader sequences. Such leader sequences can act to enhance translation. Translation leaders are known in the art and include: picornavirus leaders, for example, EMCV leader (Encephalomyocarditis 5' noncoding region), Elroy-Stein et al. (1989) *Proc. Nat Acad. Sci. USA* 86:6126-6130; potyvirus leaders, for example, TEV leader (Tobacco Etch Virus), Allison et al. (1986); MDMV leader (Maize Dwarf Mosaic Virus), *Virology* 154:9-20; human immunoglobulin heavy-chain binding protein (BiP), Macejak et al. (1991) *Nature* 353:90-94; untranslated leader from the coat protein mRNA of alfalfa mosaic virus (AMV RNA 4), Jobling et al. (1987) *Nature* 325:622-625); tobacco mosaic virus leader (TMV), Gallie et al. (1989) *Molecular Biology of RNA*, pages 237-256; and maize chlorotic mottle virus leader (MCMV) Lommel et al. (1991) *Virology* 81:382-385. See also Della-Cioppa et al. (1987) *Plant Physiology* 84:965-968. The cassette can also contain sequences that enhance translation and/or mRNA stability such as introns.

Any type of transformation can be utilized to obtain the selective ablation inducer line. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Ishida et al. (1996) *Nature Biotechnology* 14:745-750; U.S. Pat. No. 5,731,179; U.S. Pat. No. 5,591,616; U.S. Pat. No. 5,641,664; and U.S. Pat. No. 5,981,840 (maize via *Agrobacterium tumefaciens*); the disclosures of which are herein incorporated by reference.

In planta *Agrobacterium* transformation is disclosed in the following: Bechtold, N., J. Ellis, G. Pelletier (1993) C. R., *Acad Sci Paris Life Sci* 316:1194-1199; Bechtold, N., B. et al. (2000) *Genetics* 155:1875-1887; Bechtold, N. and G. Pelletier (1998) *Methods Mol Biol.* 82:259-266; Chowrira, G. M., V. Akella, and P. F. Lurquin (1995) *Mol. Biotechnol.* 3:17-23; Clough, S. J., and A. F. Bent (1998) Plant J. 16:735-743; Desfeux, C., S. J. Clough, and A. F. Bent. (2000) *Plant Physiol.* 123: 895-904; Feldmann, K. A., and M. D. Marks (1987) *Mol. Gen. Genet.* 208:1-9; Hu C.-Y., and L. Wang. (1999) In Vitro Cell Dev. Biol.-Plant 35:417-420; Katavic, V. G. W. Haughn, D. Reed, M. Martin, L. Kunst (1994) *Mol. Gen. Genet.* 245: 363-370; Liu, F., et al. (1998) Acta Hort 467:187-192; Mysore, K. S., C. T. Kumar, and S. B. Gelvin (2000) Plant J. 21:9-16; Touraev, A., E. Stoger, V. Voronin, and E. Heberle-Bors (1997) *Plant J.* 12:949-956; Trieu, A. T. et al. (2000) *Plant J.* 22:531-541; Ye, G. N. et al. (1999) *Plant J.* 19:249-257; Zhang, J U. et al. (2000) *Chem Biol.* 7:611-621. The disclosures of the above are herein incorporated by reference.

Various types of plant tissue can be used for transformation such as embryo cells, meristematic cells, leaf cells, or callus cells derived from embryo, leaf or meristematic cells. However, any transformation-competent cell or tissue can be used.

Various methods for increasing transformation frequency may also be employed. Such methods are disclosed in WO 99/61619; WO 00/17364; WO 00/28058; WO 00/37645; U.S. Ser. No. 09/496,444; WO 00/50614; US01/44038; and WO 02/04649. The disclosures of the above are herein incorporated by reference.

Transformation of maize can follow a well-established bombardment transformation protocol used for introducing DNA into the scutellum of immature maize embryos (See, e.g., Tomes et al., Direct DNA Transfer into Intact Plant Cells Via Microprojectile Bombardment. pp. 197-213 in Plant Cell, Tissue and Organ Culture, Fundamental Methods. eds. O. L. Gamborg and G. C. Phillips. Springer-Verlag Berlin Heidelberg N.Y., 1995.). Cells are transformed by culturing maize immature embryos (approximately 1-1.5 mm in length) onto medium containing N6 salts, Erikkson's vitamins, 0.69 g/l proline, 2 mg/l 2,4-D and 3% sucrose. After 4-5 days of incubation in the dark at 28° C., embryos are removed from the first medium and cultured onto similar medium containing 12% sucrose. Embryos are allowed to acclimate to this medium for 3 h prior to transformation. The scutellar surface of the immature embryos is targeted using particle bombardment. Embryos are transformed using the PDS-1000 Helium Gun from Bio-Rad at one shot per sample using 650PSI rupture disks. DNA delivered per shot averages at 0.1667 µg. Following bombardment, all embryos are maintained on standard maize culture medium (N6 salts, Erikkson's vitamins, 0.69 g/l proline, 2 mg/l 2,4-D, 3% sucrose) for 2-3 days and then transferred to N6-based medium containing a selective agent. Plates are maintained at 28° C. in the dark and are observed for colony recovery with transfers to fresh medium every two to three weeks. Recovered colonies and plants are scored based on the selectable or screenable phenotype imparted by the marker gene(s) introduced (i.e. herbicide resistance, fluorescence or anthocyanin production), and by molecular characterization via PCR and Southern analysis.

Transformation of maize can also be done using the Agrobacterium mediated DNA delivery method, as described by U.S. Pat. No. 5,981,840 with the following modifications. Agrobacteria are grown to the log phase in liquid minimal A medium containing 100 µM spectinomycin. Embryos are immersed in a log phase suspension of Agrobacteria adjusted to obtain an effective concentration of $5 \times 10^8$ cfu/ml. Embryos are infected for 5 minutes and then co-cultured on culture medium containing acetosyringone for 7 days at 20° C. in the dark. After 7 days, the embryos are transferred to standard culture medium (MS salts with N6 macronutrients, 1 mg/L 2,4-D, 1 mg/L Dicamba, 20 g/L sucrose, 0.6 g/L glucose, 1 mg/L silver nitrate, and 100 mg/L carbenicillin) with a selective agent. Plates are maintained at 28° C. in the dark and are observed for colony recovery with transfers to fresh medium every two to three weeks. Recovered colonies and plants are scored based on the selectable or screenable phenotype imparted by the marker gene(s) introduced (i.e. herbicide resistance, fluorescence or anthocyanin production), and by molecular characterization via PCR and Southern analysis.

A selectable marker can be utilized in the recovery of transformed cells. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium (the active ingredient in BASTA™), bromoxynil, imidazolinones, and 2,4-dichlorophenoxyacetate (2,4-D). For example, an herbicide resistance polynucleotide encoding glyphosate N-acetyltransferase (GAT) could be utilized with the selectable agent glyphosate. See PCT publication WO02/36782 and U.S. application Ser. No. 10/427,692. The PAT (phosphinothricin acetyltansferase) polynucleotide could be used for resistance to phosphinothricin (DeBlock et al., 1987, Engineering herbicide resistance in plant by expression of a detoxifying enzyme, *EMBO J.* 6:2513-2518). Another example is an ALS (acetolactate synthase) polynucleotide for resistance to imidazolines (Sathasivan et al., 1990, Nucleotide sequence of a mutant acetolactate synthase gene from an imidazolinone-resistant *Arabidopsis thaliana* var, *Columbia, Nucleic Acids Res.* 18:2188). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Sci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be used in the present invention.

Once haploid embryos have been identified the haploid cells, haploid embryos, haploid seeds, haploid seedlings or haploid plants can be treated with a chromosome doubling agent. Homozygous plants can be regenerated from haploid cells by contacting the haploid cells, such as haploid embryo cells, with chromosome doubling agents. The haploid cells may come in contact with the doubling agent at the time of pollination, anytime after pollination, typically 6 hours to 21 days after pollination, 6 hours to 15 days after pollination, at the mature seed stage, at the seedling stage, or at the plant stage. The haploid embryo may come in contact with the doubling agent when one sperm nucleus from a pollen grain fuses with the polar nuclei in the embryo sac to create a triploid (3N) endosperm (when the haploid embryo is formed), anytime after the pollination, typically 6 hours to 21 days after pollination, 6 hours to 15 days after pollination, or at the mature seed stage. The haploid embryo may be isolated. It may be contained within the kernel, ovule, or seed. It may also be on the ear in the case of corn, or on the spike as in the case of other grains such as wheat. The ear comprising the haploid embryo may be on the plant or isolated from the plant. The ear also may be sectioned. After chromosome doubling, the doubled haploid embryo will contain 2 copies of maternally derived chromosomes. The efficiency of the process for obtaining doubled haploid plants from haploid embryos may be greater than 10%, 20%, 30%, 50%, 60%, 70%, 80%, or 90%.

Methods of chromosome doubling are disclosed in Antoine-Michard, S. et al., Plant cell, tissue organ cult., Cordrecht, the Netherlands, Kluwer Academic Publishers, 1997, 48(3): 203-207; Kato, A., Maize Genetics Cooperation Newsletter 1997, 36-37; and Wan, Y. et al., TAG, 1989, 77:889-892. Wan, Y. et al., TAG, 1991, 81:205-211. The disclosures of which are incorporated herein by reference. Typical methods involve contacting the cells with colchicine, anti-microtubule agents or anti-microtubule herbicides, pronamide, nitrous oxide, or any mitotic inhibitor to create homozygous doubled haploid cells. The amount of colchicine used in medium is generally 0.01%-0.2% or approximately 0.05% or APM (5-225 µM). The amount of pronamide in medium is approximately 0.5-20 µM. Examples of known mitotic inhibitors are included but not limited to those indicated in Table 5. Other agents may be used with the mitotic inhibitors to improve doubling efficiency. Such agents may be dimethyl sulfoxide (DMSO), adjuvants, surfactants, and the like.

TABLE 5

| Common Name/<br>Trade name | CAS | IUPAC |
|---|---|---|
| Colchicine and Colchicine Derivatives | | |
| colchicine/<br>acetyltrimethylcol-<br>chicinic acid<br>colchicine derivatives | | (S)—N-(5,6,7,9-tetrahydro-1,2,3,10-<br>tetramethoxy-9-oxobenzo (a)<br>heptalen-7-yl) acetamide |
| Carbamates | | |
| Carbetamide | (R)-1-<br>(ethylcarbamoyl)ethyl<br>carbanilate | (2R)—N-ethyl-2-<br>[[(phenylamino)carbonyl]oxy]propanamide |
| chloropropham<br>propham | | |
| Benzamides | | |
| Pronamide/<br>propyzamide<br>tebutam | 3,5-dichloro-N-(1,1-<br>dimethylpropynyl)benzamide | 3,5-dichloro-N-(1,1-dimethyl-2-<br>propynyl)benzamide |
| Benzoic Acids | | |
| Chlorthal dimethyl<br>(DCPA),<br>Dicamba/dianat/<br>disugran (dicamba-<br>methyl) (BANVEL,<br>CLARITY) | 3,6-dichloro-o-anisic acid | 3,6-dichloro-2-methoxybenzoic<br>acid |
| Dinitroaniline chromosome doubling agents | | |
| benfluralin/benefin/<br>(BALAN) | N-butyl-N-ethyl-α,α,α-<br>trifluoro-2,6-dinitro-p-<br>toluidine | N-butyl-N-ethyl-2,6-dinitro-4-<br>(trifluoromethyl)benzenamine |
| butralin | (RS)—N-sec-butyl-4-tert-<br>butyl-2,6-dinitroaniline | 4-(1,1-dimethylethyl)-N-(1-<br>methylpropyl)-2,6-<br>dinitrobenzenamine |
| chloralin | | |
| dinitramine | N1,N1-diethyl-2,6-dinitro-<br>4-trifluoromethyl-m-<br>phenylenediamine | N3,N3-diethyl-2,4-dinitro-6-<br>(trifluoromethyl)-1,3-<br>benzenediamine |
| ethalfluralin<br>(Sonalan) | N-ethyl-α,α,α-trifluoro-N-<br>(2-methylallyl)-2,6-dinitro-<br>p-toluidine | N-ethyl-N-(2-methyl-2-propenyl)-<br>2,6-dinitro-4-<br>(trifluoromethyl)benzenamine |
| fluchloralin | N-(2-chloroethyl)-2,6-<br>dinitro-N-propyl-4-<br>(trifluoromethyl)aniline<br>or<br>N-(2-chloroethyl)-α,α,α-<br>trifluoro-2,6-dinitro-N-<br>propyl-p-toluidine | N-(2-chloroethyl)-2,6-dinitro-N-<br>propyl-4-<br>(trifluoromethyl)benzenamine |
| isopropalin | 4-isopropyl-2,6-dinitro-<br>N,N-dipropylaniline | 4-(1-methylethyl)-2,6-dinitro-N,N-<br>dipropylbenzenamine |

TABLE 5-continued

| Common Name/ Trade name | CAS | IUPAC |
|---|---|---|
| methalpropalin | α,α,α-trifluoro-N-(2-methylallyl)-2,6-dinitro-N-propyl-p-toluidine | N-(2-methyl-2-propenyl)-2,6-dinitro-N-propyl-4-(trifluoromethyl)benzenamine |
| nitralin | 4-methylsulfonyl-2,6-dinitro-N,N-dipropylaniline | 4-(methylsulfonyl)-2,6-dinitro-N,N-dipropylbenzenamine |
| oryzalin (SURFLAN) | 3,5-dinitro-N4,N4-dipropylsulfanilamide | 4-(dipropylamino)-3,5-dinitrobenzenesulfonamide |
| pendimethalin (PROWL) | N-(1-ethylpropyl)-2,6-dinitro-3,4-xylidine | N-(1-ethylpropyl)-3,4-dimethyl-2,6-dinitrobenzenamine |
| prodiamine | 5-dipropylamino-α,α,α-trifluoro-4,6-dinitro-o-toluidine or 2,6-dinitro-N1,N1-dipropyl-4-trifluoromethyl-m-phenylenediamine | 2,4-dinitro-N3,N3-dipropyl-6-(trifluoromethyl)-1,3-benzenediamine |
| profluralin | N-cyclopropylmethyl-α,α,α-trifluoro-2,6-dinitro-N-propyl-p-toluidine or N-cyclopropylmethyl-2,6-dinitro-N-propyl-4-trifluoromethylaniline | N-(cyclopropylmethyl)-2,6-dinitro-N-propyl-4-(trifluoromethyl)benzenamine |
| trifluralin (TREFLAN, TRIFIC, TRILLIN) | α,α,α-trifluoro-2,6-dinitro-N,N-dipropyl-p-toluidine | 2,6-dinitro-N,N-dipropyl-4-(trifluoromethyl)benzenamine |
| Phosphoroamidates | | |
| APM (Amiprofos methyl); amiprophos-methyl | | |
| Butamifos | O-ethyl O-6-nitro-m-tolyl (RS)-sec-butylphosphoramidothioate | O-ethyl O-(5-methyl-2-nitrophenyl) (1-methylpropyl)phosphoramidothioate |
| Pyridines | | |
| Dithiopyr | | |
| Thiazopyr | methyl 2-difluoromethyl-5-(4,5-dihydro-1,3-thiazol-2-yl)-4-isobutyl-6-trifluoromethylnicotinate | methyl 2-(difluoromethyl)-5-(4,5-dihydro-2-thiazolyl)-4-(2-methylpropyl)-6-(trifluoromethyl)-3-pyridinecarboxylate |

The chromosome doubling agent may come in contact with the embryo at various times. If the embryo is isolated the doubling agent may come in contact immediately after isolation and before germination. If the embryo is contained within the seed, it may come in contact with the doubling agent anytime after pollination and before dry down. The embryo whether it is isolated or not may come in contact with the doubling agent any time between 6 hours after pollination and 21 days after pollination. The duration of contact between the chromosomal doubling agent may vary. Contact may be from less than 24 hours to about a week. The duration of contact is generally from about 24 hours to 2 days.

Methods provided may or may not go through a callus formation stage. The haploid embryos may be placed on a "non-callus" promoting medium. The term "non-callus promoting medium" refers to a medium that does not support proliferation of dedifferentiated masses of cells or tissue. A preferred "non-callus promoting medium" is used for embryo rescue, containing typical salt and vitamin formulations well known in the art. Such embryo rescue, or embryo culture, media contain little or no auxin [for review see Raghaven, V., 1966. Biol. Rev. 41:1-58]. Embryo maturation medium also represents another preferred "non-callus promoting medium". Embryo maturation medium is used to promote development of in vitro cultured embryos, preventing precocious germination, and typically contain standard salt/vitamin formulations (depending on the species), increased sugar levels and/or exogenously added abscisic acid, with little or no auxin. Another type of medium is used for shoot culture, or multiple shoot proliferation. This multiple-shoot medium can again contain little or reduced auxin, but instead contain elevated levels of cytokinin that promote meristem proliferation and growth.

An auxin is defined as an endogenous plant hormone such as indole acetic acid (IAA), derivatives of IAA such as indole-3-buteric acid, as well as compounds with auxin-like activity such as 2,4-D; picloram; dicamba; 3,4-D; 2,4,5-T and naphthalene acetic acid (NAA).

A cytokinin is defined as a naturally occurring plant hormone such as 2-isopentynel adenine (2IP), zeatin and dihydrozeatin, or a synthetic compound with cytokinin-like activity such as kinetin and BAP (beynzylaminopurine).

Haploid cells from embryos, seeds, plants, etc. can be identified by several methods, such as, by chromosomal counts, measuring the length of guard cells, or by use of a Flow Cytometer.

Molecular markers or quantitative PCR can be used to determine if a tissue or plant is made of doubled haploid cells or is made of diploid cells (cells obtained through normal pollination).

Haploid embryos which are derived by any of the above techniques can be cultured to regenerate a whole plant. Such techniques are called embryo rescue. Embryo rescue media can comprise certain phytohormones and energy sources or just energy sources. The growth medium may also contain a selection agent such as a biocide and/or herbicide. This selection agent can be used to indicate a marker which has been introduced through the transformation process. For transformation and regeneration of maize see, Gordon-Kamm et al., The Plant Cell 2:603-618 (1990).

The methods provided can be practiced with any plant. Such plants include but are not limited to Zea mays (also identified as corn or maize), soybean, oilseed Brassica, alfalfa, rice, rye, sorghum, sunflower, tobacco, potato, peanuts, cotton, sweet potato, cassava, sugar beets, tomato, oats, barley, and wheat.

Generation of embryos into plants is well known in the art. Embryo rescue techniques can be used to generate immature doubled haploid embryos into plants (Recent Research Developments in Genetics & Breeding. Vol. 1, Part II, 287-308 2004). The disclosure of which is herein incorporated by reference.

The temperature at which the methods can be performed can vary. The methods provided can be practiced at any temperature that does not kill a plant cell or plant or from about 16 degrees Celsius to 32 degrees Celsius.

Provided are methods of producing haploid embryos and non-viable diploid embryos on a maize plant. The method includes but is not limited to producing about 3% or greater, about 5% or greater, or about 10% or greater viable haploid embryos. For calculating the percentage, the total number of embryos is determined by adding the number of haploid embryos to the number of embryos that did not develop properly. The non-viable diploid embryos may be selected against any time after pollination. The method includes but is not limited to selection at 7-15 days, 10-21 days, or at the time the haploid seed is fully mature, for example during or after dry down.

Provided are methods of selecting for haploid maize embryos by pollinating a maize ear with the pollen from an inducer maize line. The inducer line has a gene that is expressed in the embryo and can be lethal. At another location in the genome the inducer maize line has a gene that prevents pollen transmission. The gene that prevents pollen transmission is closely linked to a gene that when expressed in the embryo inhibits the lethality of the gene at the first location. Thus, when the maize ear is pollinated by this inducer line there is no transmission of pollen that contains the gene that prevents the lethal effects of the lethal gene. Only pollen with the gene that is lethal to embryo development is transmitted. When this pollen is used and normal fertilization occurs resulting in a diploid embryo, the embryo will not develop because of the transmission of the lethal gene. When this pollen is used and irregular fertilization occurs it results in a haploid embryo. This haploid embryo will continue to develop. Because of the ablation of the diploid embryos, haploid embryos will easily be selected at an early stage of development. Having the lethal gene and the inhibitor gene at different locations in the genome, for example having the genes unlinked, allows the genes to segregate so that an adequate amount of pollen comprising the lethal gene is produced. The gene that prevents pollen transmission is closely linked to, or adjacent to, the gene that inhibits embryo ablation.

Another method provided is the development of an improved inducer line, called a selective ablation inducer line. A maize inducer line can be transformed with two different expression cassettes. A first expression cassette includes a polynucleotide that when expressed in the embryo is lethal to the embryo or prevents the embryo from developing normally. A second expression cassette includes a polynucleotide that prevents viable or transmissible pollen from developing and a polynucleotide that when expressed in the embryo prevents death or abnormal growth that would be caused by the polynucleotide on the first expression cassette. The transformation process can be by various methods for example particle bombardment or agrobacterium infection. The transformation process with the two cassettes may be done simultaneously or sequentially with the cassette comprising the polynucleotide to prevent embryo lethality being introgressed into the plant cell first. The expression cassettes need to segregate in the gamete, therefore it is preferred that the two expression cassettes not be tightly linked. As part of the method, any maize line may be transformed with the first, or first and second expression cassette. The first and/or second expression cassettes may be used to transform one or two maize plants. The expression cassettes can then be transferred simultaneously or sequentially into a maize inducer line by crossing. The method can include backcrossing one or all trangenes into a maize inducer line. The repressor could be replaced and segregated out.

In any of the methods disclosed the inhibition described can be by various mechanisms. For example, the transcription of the lethal polynucleotide may be prevented. This type of inhibition could be achieved by using a tet repressor polynucleotide that expresses a protein that binds to the lethal gene and inhibits expression. Other types of prevention of lethality may be at the RNA or protein stage for example, anti-sense RNA, hair-pins, and other mechanisms for gene silencing.

In any of these methods and products, the gene that prevents pollen transmission can be a lethal gene with a pollen specific promoter. For example the gene can express alpha-amylase (Gene Bank L25805), Plant Physiology 105(2):759-760 (1994)) and it can be controlled with a PG47 promoter (U.S. Pat. No. 5,412,085; U.S. Pat. No. 5,545,546; Plant J. 3(2): 261-271 (1993)). In any of these methods and products the expression of the polynucleotide that causes ablation and the polynucleotide that inhibits ablation can be controlled by various types of promoters. For example the promoter may be a constitutive promoter, an inducible promoter, or a tissue preferred promoter such as an embryo preferred promoter. It would be most efficient if the promoter that drives the polynucleotide that causes ablation of the embryo would not express in endosperm. Or if the promoter is expressed in the endosperm the expression would be low enough that one could still determine a difference in growth between the diploid seed (normal fertilization) and the haploid seed. An example of embryo preferred promoter is led.

The invention disclosed includes a maize inducer line comprising the two expression cassettes as described.

All publications and patent applications mentioned in this specification are herein incorporated by reference to the same extent as if each individual publication or patent application was specifically and individually indicated to be incorporated by reference.

The following examples are offered by way of illustration and not by way of limitation.

EXAMPLES gat—genes encoding glyphosate N-acetyltransferase (GAT). See PCT publication WO02/36782 and U.S. application Ser. No. 10/427,692.

lec1—indicates a leafy cotyledon 1 transcriptional activator polynucleotide. See U.S. patent application Ser. No. 09/435,054. lec1 promoter is characterized in U.S. Pat. No. 7,122,658.

moCah—is a maize optimized gene that encodes for the Myrotheciurn verrucaria cyanamide hydratase protein [CAH] that can hydrate cyanamide to non-toxic urea.

pinII—indicates potato proteinase inhibitor. See Ryan (1990) Ann. Rev. Phytopath. 28:425-449; Duan et al. (1996) Nature Biotechnology 14:494-498.

Pro—indicates a promoter sequence.

Term—indicates a terminator sequence.

Ubi Pro—indicates a ubiquitin promoter. See Christensen et al. (1989) Plant Mol. Biol. 12:619-632 and Christensen et al. (1992) Plant Mol. Biol. 18:675-689) Ubi1ZM Pro-indicates a ubiquitin maize promoter.

Example 1

Seeds from haploid inducer lines, such as Stock 6, RWS, KEMS, KMS or ZMS, are planted and self or sib pollinated at flowering. The ears are surface sterilized in 30% Clorox bleach plus 0.5% Micro detergent for 20 minutes, and rinsed two times with sterile water.

For Agrobacterium-mediated transformation of maize the method of Zhao is employed essentially as described in U.S. Pat. No. 5,981,840, the contents of which are hereby incorporated by reference. Embryos (generally about 7-14 days after pollination) are isolated from a maize plant and the embryos are contacted with a suspension of Agrobacterium, where the bacteria are capable of transferring the nucleotide sequences of interest to at least one cell of at least one of the embryos. The Agrobacterium comprises the following expression cassette.

Construct C:
ZM-lec1 promoter: UB1ZMintron:barstar:pinII 3'terminator—ZM-PG47 promoter:ZM-BT1 transit peptide:ZM-alpha-amylase1:ZM-IN2-1 3' terminator—UB1ZM promoter: 5'UTR intron:GAT:PINII 3' terminator.

In this step the embryos are typically immersed in an Agrobacterium suspension for the initiation of inoculation. Preferably, the Agrobacterium suspension contains 100 µM acetosyringone. The embryos are co-cultured for a time with the Agrobacterium.

Generally the embryos are cultured on solid medium following the infection step. Following this co-cultivation period an optional "resting" step lasting 6-7 days is contemplated. In this resting step, the embryos are incubated in the presence of at least one antibiotic known to inhibit the growth of Agrobacterium without the addition of a selective agent for plant transformants. Next, inoculated embryos are cultured on solid medium containing a selective agent for GAT, which is the herbicide glyphosate (GAT-genes encoding glyphosate N-acetyltransferase (GAT). See PCT publication WO02/36782 and U.S. application Ser. No. 10/427,692).

After being placed on the selection media the growing transformed callus is transformed with a second cassette, Construct D. This time using particle bombardment.

Construct D:
ZM-lec1 promoter:Potato LS intron:barnase:pinII 3'terminator—UB1ZM promoter:5'UTR intron:moPAT:PINII 3' terminator.

This plasmid DNA is precipitated onto 1.1 µm (average diameter) tungsten pellets using a CaCl2 precipitation procedure as follows: 100 µl prepared tungsten particles in water, 10 µl (1 µg) DNA in TrisEDTA buffer (1 µg total), 100 µl 2.5 M CaCl$_2$, 10 µl 0.1 M spermidine.

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 µl 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment. The sample plates are bombarded at level #4 in particle gun #HE34-1 or #HE34-2. All samples receive a single shot at 650 PSI, with a total of ten aliquots taken from each tube of prepared particles/DNA.

Following bombardment, the callus is kept on 560Y medium for 2 days, then transferred to selection medium containing the selection agent for the PAT gene, bialophos, and subcultured every 2 weeks.

After approximately 10 weeks of selection, selection-resistant callus clones are transferred to regeneration medium to initiate plants. Following somatic embryo maturation (2-4 weeks), well-developed somatic embryos are transferred to medium for germination and transferred to the lighted culture room. Approximately 7-10 days later, developing plantlets are transferred to hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for the genotype and/or phenotype of interest.

Bombardment medium comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H20 following adjustment to pH 5.8 with KOH); 2.0 g/l Gelrite (added after bringing to volume with D-I H20); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H20 following adjustment to pH 5.8 with KOH); 3.0 g/l Gelrite (added after bringing to volume with D-I H20); and 0.85 mg/l silver nitrate and selection agent (both added after sterilizing the medium and cooling to room temperature).

Example 2

Production of Haploid Embryos

After an ablation haploid inducer line is produced as indicated in Example 1. The inducer line can be used to produce haploid embryos. This can be achieved through the growing of F1 corn seed. For example a corn breeder wanting to produce a superior inbred with the best characteristics from elite inbred line A and elite inbred line B crosses the two inbreds to form F1 hybrid seed. This F1 seed is grown along with the ablation inducer line. The timing of the planting is such that the pollen of the ablation inducer line is ready at the silking time of the F1 hybrid seed. The silks of the F1 plants are pollinated with the ablation inducer line pollen. This can be achieved by planting alternate rows of the F1 and the inducer line, and various combinations thereof with the F1, or female, plants being detasseled before pollination. The crosses can also be done by shoot bagging and controlling pollination by hand pollinating.

After the seed has matured the seed can be harvested and the only viable seed will be the haploid seed. The haploid seed is then planted and undergoes chromosome doubling using a chromosomal doubling agent such as pronamide.

Example 3

Transformation and Regeneration of Transgenic Inducer Maize Plants

Hi-II maize seeds are planted. The ears at 9-12 days after pollination are harvested surface sterilized in 30% Clorox bleach plus 0.5% Micro detergent for 20 minutes, and rinsed two times with sterile water. The embryos are isolated from ears using a scalpel. Embryos are contacted with a suspension of *Agrobacterium*, where the bacteria are capable of transferring the nucleotide sequences of interest to at least one cell of at least one of the embryos. In this example the embryos are co-transformed with 2 Agrobacteria.

One *Agrobacterium* comprises the following expression cassette.
Construct E:
ZM-lec1 promoter: UB1ZMintron:barstar:pinII 3'terminator—ZM-PG47 promoter:ZM-BT1 transit peptide:ZM-alpha-amylase1:ZM-IN2-1 3' terminator—UB1ZM promoter: 5'UTR intron:GAT:PINII 3' terminator.

The second *Agrobacterium* comprises the following expression cassette.
Construct F:
ZM-lec1 promoter:Potato LS intron:barnase:pinII 3'terminator—UB1ZM promoter:5'UTR intron:moPAT:PINII 3' terminator.

The barnase gene includes an intron for the purpose of preventing expression of barnase in the *Agrobacterium*.

The tissue culture media and process is the same as described above with the selection agent, bialophos. Callus that only comprises Construct E will be selected against with the use of bialophos. Callus that only comprises Construct F will not regenerate because the barstar construct is not available to prevent the toxicity of the barnase.

Plants will be regenerated that comprise Constructs E and F. These plants will be used to backcross both constructs into a maize haploid inducer line. During the backcross process the co-transformed lines will evaluated to determine the linkage between the constructs. The closer the constructs are linked the less transmission of the barnase polynucleotide through the pollen will occur because it will segregate with the alpha-amylase polynucleotide expressed in the pollen making the pollen non-viable.

When a cross is made with unlinked constructs, the diploid embryos are eliminated because the barstar-containing construct is not transmitted through pollen, and they only inherit barnase.

Barstar and barnase are both expressed in early embryogenesis on separate, unlinked transgenes in the haploid inducer line. Thus, the haploid inducer line can be maintained.

Example 4

Transformation and Regeneration of Transgenic Inducer Maize Plants Using *Agrobacterium* Comprising Two T-DNA Constructs One *Agrobacterium* comprises the following 2 expression cassettes.
RB:ZM-lec1 promoter: UB1ZMintron:barstar:pinII 3'terminator—ZM-PG47 promoter:ZM-BT1 transit peptide:ZM-alpha-amylase1:ZM-IN2-1 3' terminator—UB1ZM promoter: 5'UTR intron:GAT:PINII 3' terminator:LB
RB:ZM-lec1 promoter:Potato LS intron:barnase:pinII 3'terminator—UB1ZM promoter:5'UTR intron:moPAT:PINII 3' terminator:LB Transformation with *Agrobacterium* containing cassettes can increase the efficiency of producing stably transformed plants comprising the two cassettes at locations in the genome that are not linked (Miller et al. Transgenic Research 11:381-396, 2002. High efficiency transgene segregation in co-transformed maize plants using an *Agrobacterium tumefaciens* 2 T-DNA binary system.)

Other than the vector, the process to obtain a maize ablation haploid inducer line can be the same as indicated in Example 3.

What is claimed is:
1. A method of selecting for haploid maize embryos comprising:
   a) pollinating a first maize plant with the pollen from a maize haploid inducer line to produce embryos wherein said maize haploid inducer line comprises an embryo expressed lethal polynucleotide operably linked to an embryo-preferred promoter, a non-transmission pollen polynucleotide operably linked to a pollen-specific promoter, and an embryo expressed inhibitor polynucleotide that prevents the lethality of said embryo expressed lethal polynucleotide wherein said non-transmission pollen polynucleotide and said embryo expressed inhibitor polynucleotide are linked so that they will segregate together;
b) producing haploid embryos and non-viable diploid embryos; and
c) selecting haploid maize embryos;
further wherein said embryo expressed lethal polynucleotide is barnase and said embryo expressed inhibitor polynucleotide is barstar.

2. A transgenic maize haploid inducer line comprising a first and second expression cassette, wherein said first expression cassette comprises a polynucleotide that is lethal to embryos operably linked to an embryo-preferred promoter and wherein said second cassette comprises a non-transmission pollen polynucleotide operably linked to a pollen-specific promoter and a polynucleotide that inhibits the lethality of said polynucleotide that is lethal to embryos, wherein said polynucleotide that is lethal to embryos is a barnase polynucleotide and said polynucleotide that inhibits the lethality of said polynucleotide that is lethal to embryos is a barstar polynucleotide.

3. The transgenic maize haploid inducer line of claim 2 wherein said polynucleotide that is lethal to embryos is operably linked to a lec1 promoter.

4. A transgenic maize haploid inducer line comprising a first and second expression cassette wherein; said first expression cassette comprises a barnase polynucleotide that is operably linked to a lec1 promoter and is lethal to embryos and wherein; said second cassette comprises a barstar polynucleotide that inhibits the lethality of said polynucleotide that is lethal to embryos and wherein, said second expression cassette also comprises an alpha-amylase polynucleotide operably linked to a PG47 promoter wherein expression of said alpha-amylase polynucleotide operably linked to a PG47 promoter does not allow pollen transmission.

* * * * *